United States Patent
Thorne et al.

(10) Patent No.: US 12,405,327 B2
(45) Date of Patent: *Sep. 2, 2025

(54) OMNIDIRECTIONAL MRI CATHETER RESONATOR AND RELATED SYSTEMS, METHODS AND DEVICES

(71) Applicant: Regents of the University of California, Oakland, CA (US)

(72) Inventors: Bradford Thorne, San Francisco, CA (US); Prasheel Lillaney, Redwood City, CA (US); Aaron Losey, San Francisco, CA (US); Steve Hetts, Hillsborough, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/207,573

(22) Filed: Jun. 8, 2023

(65) Prior Publication Data

US 2023/0408606 A1 Dec. 21, 2023

Related U.S. Application Data

(63) Continuation of application No. 15/305,993, filed as application No. PCT/US2015/027624 on Apr. 24, 2015, now Pat. No. 11,714,143.

(Continued)

(51) Int. Cl.
| | |
|---|---|
| *G01R 33/28* | (2006.01) |
| *A61B 5/055* | (2006.01) |
| *A61B 5/06* | (2006.01) |
| *A61M 25/01* | (2006.01) |
| *A61B 18/00* | (2006.01) |

(Continued)

(52) U.S. Cl.
CPC ............ *G01R 33/287* (2013.01); *A61B 5/055* (2013.01); *A61B 5/062* (2013.01); *A61B 5/066* (2013.01); *A61M 25/0108* (2013.01); *A61M 25/0127* (2013.01); *A61B 18/00* (2013.01);

(Continued)

(58) Field of Classification Search
CPC ......... A61B 5/066; A61B 5/062; A61B 5/055; A61B 2090/3954; G01R 33/287; A61M 25/0127

See application file for complete search history.

(56) References Cited

U.S. PATENT DOCUMENTS

| | | | |
|---|---|---|---|
| 6,005,197 A | 12/1999 | Kola | |
| 6,171,240 B1 * | 1/2001 | Young | ................. G01R 33/287 324/318 |

(Continued)

OTHER PUBLICATIONS

Ellersiek, D. "A monolithically fabricated flexible resonsant circut for catheter tracking in magnetic resonance imaging." Sensors and Actuators B 144 (2010) 432-436 (Year: 2010).

(Continued)

*Primary Examiner* — Keith M Raymond
*Assistant Examiner* — Milton Truong
(74) *Attorney, Agent, or Firm* — DENTONS DAVIS BROWN PC; Matthew Warner-Blankenship (57) ABSTRACT

The disclosed apparatus, systems and methods relate to interventional magnetic resonance imaging (iMRI). More specifically, clinical applications of the disclosed include magnetic resonance (MR) guided procedures such as endovascular interventions, percutaneous biopsies or deep brain stimulation.

20 Claims, 7 Drawing Sheets

Related U.S. Application Data (60) Provisional application No. 61/983,889, filed on Apr. 24, 2014.

(51) Int. Cl.
  *A61B 18/14* (2006.01)
  *A61B 90/00* (2016.01)
  *A61N 1/05* (2006.01)

(52) U.S. Cl.
  CPC ... *A61B 18/1492* (2013.01); *A61B 2090/3954* (2016.02); *A61N 1/0534* (2013.01)

(56) References Cited

U.S. PATENT DOCUMENTS

| | | | | |
|---|---|---|---|---|
| 8,082,021 | B2* | 12/2011 | Hyde | A61B 5/06 607/101 |
| 2003/0028095 | A1 | 2/2003 | Tulley | |
| 2005/0251031 | A1 | 11/2005 | Smith | |
| 2006/0264049 | A1 | 11/2006 | Ittel | |
| 2009/0216109 | A1* | 8/2009 | Karmarkar | A61B 5/4839 604/500 |
| 2010/0249572 | A1* | 9/2010 | Weiss | G01R 33/287 600/410 |
| 2010/0256480 | A1 | 10/2010 | Bottomley | |
| 2011/0079423 | A1* | 4/2011 | Zhao | A61N 1/056 336/208 |
| 2012/0146667 | A1* | 6/2012 | Syms | G01R 33/34084 324/629 |
| 2012/0235633 | A1 | 9/2012 | Kesler et al. | |

OTHER PUBLICATIONS

Den Kamp, O. "Analysis and design of intravascular MR antennas.", 2003 https://pure.tue.nl/ws/portalfiles/46792658/560177-1.pdf (Year: 2003).

* cited by examiner

$$CNR = \frac{|S_1 \ S_2|}{\sigma_0}$$

OMNIDIRECTIONAL MRI CATHETER RESONATOR AND RELATED SYSTEMS, METHODS AND DEVICES

CROSS-REFERENCE TO RELATED APPLICATION(S)

This application is a continuation of U.S. patent application Ser. No. 15/305,993, filed on Oct. 21, 2016, which is a National Stage Entry of PCT/US15/27624, filed Apr. 24, 2015 which claims priority to U.S. Provisional Application 61/983,889, filed Apr. 24, 2014 and entitled "Omnidirectional MRI Catheter Resonator," which is hereby incorporated herein by reference in its entirety.

GOVERNMENT SUPPORT

This invention was made with government support under Grant No. EB012031 awarded by the National Institutes of Health. Accordingly, the United States government may have certain rights in the invention.

TECHNICAL FIELD

The disclosure relates to various marker devices and related systems and methods for use in magnetic resonance guided endovascular procedures.

BACKGROUND

The promise of magnetic resonance (MR) guided endovascular procedures remains largely unrealized. A safe and appropriately sized apparatus for catheter tracking has yet to be described to date. While markers have been previously described; shortcomings in size, efficacy and safety have precluded clinical application. There is a need in the art for improved methods and devices for guiding endovascular procedures via magnetic resonance.

BRIEF SUMMARY

Discussed herein are various systems, devices and methods relating to interventional magnetic resonance imaging (iMRI) markers. Specific clinical applications include magnetic resonance (MR) guided procedures such as endovascular interventions, percutaneous biopsies or deep brain stimulation.

In Example 1, an omnidirectional MRI resonant marker comprises a tunable capacitor and a conductor formed into a conductor coil. The conductor coil is operably coupled to the tunable capacitor, wherein the conductor coil is configured to be associated with a medical device.

Example 2 relates to the resonant marker according to Example 1, wherein the conductor coil comprises a double helix configuration or a solenoid configuration.

Example 3 relates to the resonant marker according to Example 1, wherein the tunable capacitor is configured to be tunable by modifying the capacitor structurally or chemically.

Example 4 relates to the resonant marker according to Example 1, further comprising an outer sealant layer disposed over the tunable capacitor and the conductor coil.

Example 5 relates to the resonant marker according to Example 1, further comprising a resistor operably coupled to the tunable capacitor and the conductor coil.

Example 6 relates to the resonant marker according to Example 1, wherein at least one portion of the conductor coil is perpendicular to a magnetic resonance field.

Example 7 relates to the resonant marker according to Example 1, wherein the tunable capacitor and the conductor coil are formed from a flexible circuit laminate.

Example 8 relates to the resonant marker according to Example 7, further comprising an insulating layer on one side of the conductor.

Example 9 relates to the resonant marker according to Example 1, wherein the tunable capacitor is integral with the conductor coil.

Example 10 relates to the resonant marker according to Example 1, wherein the medical device is a catheter.

In Example 11, an omnidirectional MRI resonant marker comprises a tunable capacitor and a conductor formed into a conductor coil. The tunable capacitor is configured to be tunable by modification of the capacitor. The conductor coil is operably coupled to the tunable capacitor, wherein the conductor coil comprises a double helix configuration and is configured to be associated with a catheter.

Example 12 relates to the resonant marker according to Example 11, wherein the conductor coil is configured to be positioned around the catheter.

Example 13 relates to the resonant marker according to Example 11, wherein the conductor coil is configured to be disposed within a wall of the catheter.

Example 14 relates to the resonant marker according to Example 11, further comprising an outer sealant layer disposed over the tunable capacitor and the conductor coil.

Example 15 relates to the resonant marker according to Example 11, further comprising a resistor operably coupled to the tunable capacitor and the conductor coil.

Example 16 relates to the resonant marker according to Example 11, wherein at least one portion of the conductor coil is perpendicular to a magnetic resonance field.

Example 17 relates to the resonant marker according to Example 11, wherein the modification of the tunable capacitor is removal of a portion of the capacitor.

Example 18 relates to the resonant marker according to Example 11, wherein the tunable capacitor is integral with the conductor coil.

In Example 19, an omnidirectional MRI trackable catheter comprises a catheter body, a conductor formed into a double helix conductor coil, and a tunable capacitor operably coupled to and integral with the conductor coil. The conductor coil is associated with the catheter body, wherein at least one portion of the conductor coil is perpendicular to a magnetic resonance field. The tunable capacitor is configured to be tunable by modification of the capacitor.

Example 20 relates to the trackable catheter according to Example 19, further comprising an outer sealant layer disposed over the tunable capacitor and the conductor coil.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

DETAILED DESCRIPTION

The disclosed systems, devices and methods relate to an orientation-independent resonant structure (also referred to herein as a "marker" or "resonator") that creates bright and highly localized signal enhancement during the magnetic resonance imaging (MRI) process. The embodiments disclosed or contemplated herein relate to a unique design which makes it a desirable marker for placement on catheters or other devices being used in procedures being performed under MRI guidance. In certain implementations, the device is a miniature resonant structure for use as a bright marker on endovascular catheters. Alternatively, the device is an MR-compatible catheter with a safe, highly localized, non-destructive bright marker suitable for both X-ray fluoroscopy and interventional MRI ("iMRI"). Certain embodiments can be adapted to work with many pre-existing and developing MR therapies with low startup and material costs.

Figure 1A:
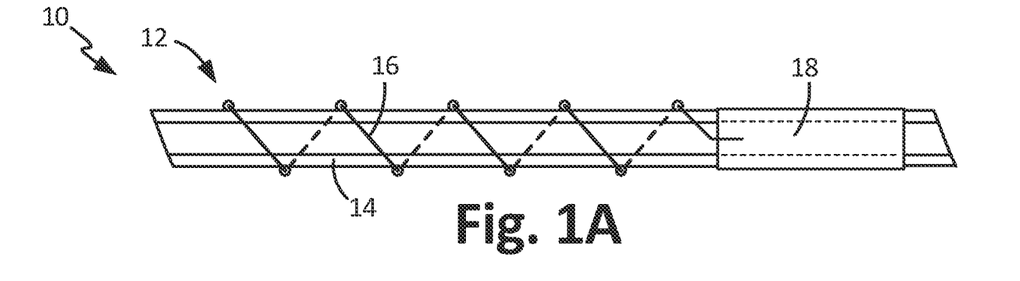
FIG. 1A is a side view of an assembly having a resonant marker positioned around a catheter, according to one embodiment.
Figure 1B:
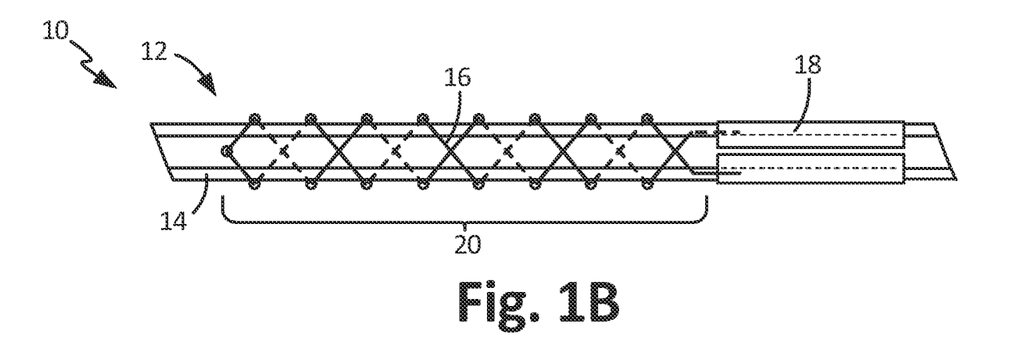
FIG. 1B is a top view of the assembly of FIG. 1A.

FIGS. 1A and 1B depict an exemplary embodiment of an assembly 10 having a resonant marker 12 constructed on an endovascular catheter 14. FIG. 1A shows a side view of the catheter 14 with the marker 12, while FIG. 1B shows a top view. In this embodiment, the marker 12 is an omnidirectional passive MRI resonant marker 12. The marker 12 has a conductor 16 (also referred to herein as a "trace" and "conductive trace") that forms a conductor coil 20 (also referred to herein as a "coil" and an "inductive coil") and a capacitor 18.

The conductor 16 is positioned around the catheter 14 to form the coil 20. The conductor 16 in this specific implementation is an insulated wire 16, and more specifically an insulated copper wire 16, that is wound around the catheter 14 to create a double helix coil 20. Alternatively, the conductor 16 can be made of copper, various alloys, including alloys containing copper, silver, graphene, Nichrome, Nitinol or any other known conductive material that can be used in a resonant marker. In one specific example, the conductor 16 is 34 AWG (d=0.160 mm) insulated wire 16. While the conductor 16 can be wound into the shape of a double helix coil 20 as shown, the conductor 16 can also be wound or otherwise positioned around the catheter 14 in other coil configurations as well, including, for example, a single helix, a compact or expanded solenoid, or a saddle-back-like configuration. Further, in this particular instance, the conductor 16 is wound at a 45° angle around the catheter 14. Alternatively, the conductor 16 can be disposed around the catheter 14 at an angle ranging from about 30° to about 60°. In a further alternative, the conductor 16 can be disposed around the catheter 14 at an angle ranging from about 0° to about 90°.

According to one implementation, the double helix coil configuration is effective because at least some portion of the wire 16 (such as one loop of the coil 20, for example) is perpendicular to the radio frequency (RF), $B_1$, field directed perpendicular to the longitudinal axis, $B_0$. The applied $B_1$ field on the double helical coil 20 during imaging induces a current and the resulting resonance creates high localized signal enhancement. The perpendicular positioning of the wire 16 in relation to the field ensures that the coil 20 can be captured by the imaging system, thereby making it possible for the catheter 14 and coil 20 to be positioned in any position or direction and still be captured by the imaging system (hence: omnidirectional).

The conductor 16 is coupled to the capacitor 18. More specifically, in certain embodiments, the conductor 16 is soldered to the capacitor 18. According to this specific embodiment, the capacitor 18 is a custom parallel plate capacitor 18 using DuPont's® Pyralux® AP polyimide double sided copper clad laminate (specifically AP 7164E). The "sandwiched" configuration is comprised of a thin polyimide sheet sandwiched or otherwise positioned between two copper sheets. More specifically, this specific capacitor 18 is comprised of one 25.4 µm thick polyimide sheet sandwiched between two 12.7 µm copper sheets. Alternatively, the dielectric of the capacitor 18 can be made of polypropylene, Mylar, or any other dielectric material, and can have a thickness ranging from less than 1 µm to more than 100 µm. The dielectric may be a polymer as listed above, or alternatively can be an adhesive, an air gap, an electrolyte, or any other non- or minimally-conductive material. In one implementation, the capacitor 18 can be a flexible capacitor. In addition to the parallel plate configuration, the capacitor 18 can alternatively express various geometries including, but not limited to, interdigital or multi-layered configurations. Further, the capacitor 18 can have a multilayer configuration or any other known configuration.

In alternative embodiments, the conductor coil 20 is made of or formed out of other structures other than a wire. For example, the coil 20 can be printed with conductive paste (silver or some other known conductor) or photo-etched from a thin copper-polyimide laminate. The resulting structure of this coil 20 embodiment is scalable and has a minimal cross section, thus increasing flexibility and facilitating integration into the walls of catheters and other devices.

In this specific example, the catheter 14 is a 1.69 mm clinical grade endovascular catheter. Alternatively, the marker 12 and any other marker or resonator embodiment disclosed or contemplated herein can be positioned around any known endovascular catheter for use in a human patient, provided that any in-wall conductive wires do not interfere with the marker's operation. In a further alternative, the marker 12 and any marker or resonator embodiment disclosed or contemplated herein can be positioned around any known catheter for use in a human patient, such as, for example, any urinary catheter.

Figure 2A:
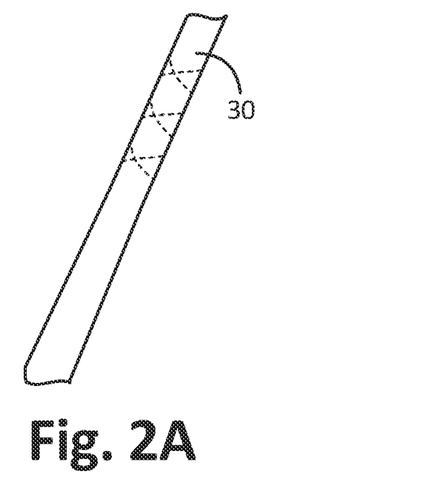
FIG. 2A is a magnified perspective view of a portion of an assembly having a resonant marker positioned around a catheter with an exterior coating over the assembly, according to one embodiment.
Figure 2B:
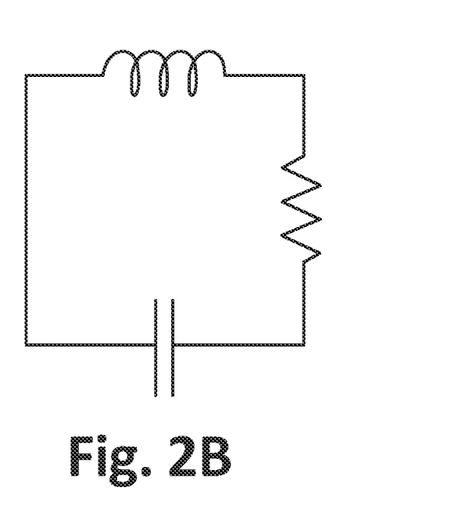
FIG. 2B is a schematic of a first order resonant marker, according to one embodiment.

As shown in FIGS. 2A-2B, in certain embodiments, a coating or layer 30 can be applied over the assembly 10. For example, in one embodiment, the coating 30 is a polyurethane layer 30 that is applied over the assembly 10. Alternatively, the coating 30 can be heat shrink tubing 30. According to some embodiments, the external coating 30 is a waterproofing layer 30 that provides an external fluidic seal to prevent or reduce access of fluid to the assembly 10. Alternatively, the layer 30 can also help to prevent or reduce movement of the coiled wire 16. In one exemplary embodiment, the protective coating 30 was applied and cured at 110° C.

Figure 3A:
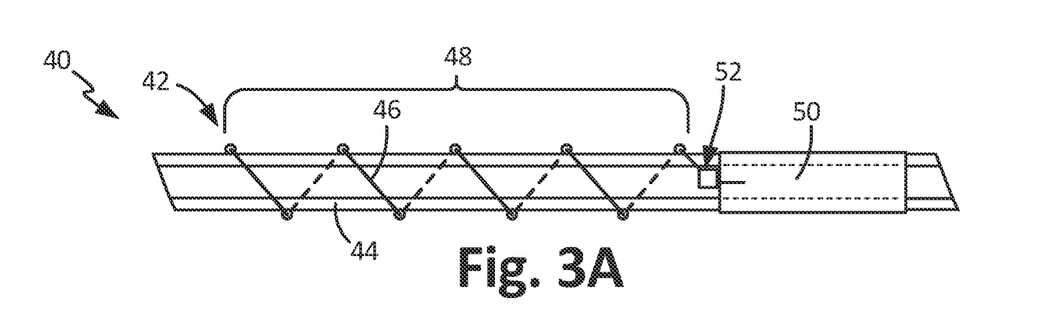
FIG. 3A is a side view of an assembly having a resonant marker with a resistor, wherein the marker is positioned around a catheter, according to one embodiment.
Figure 3B:
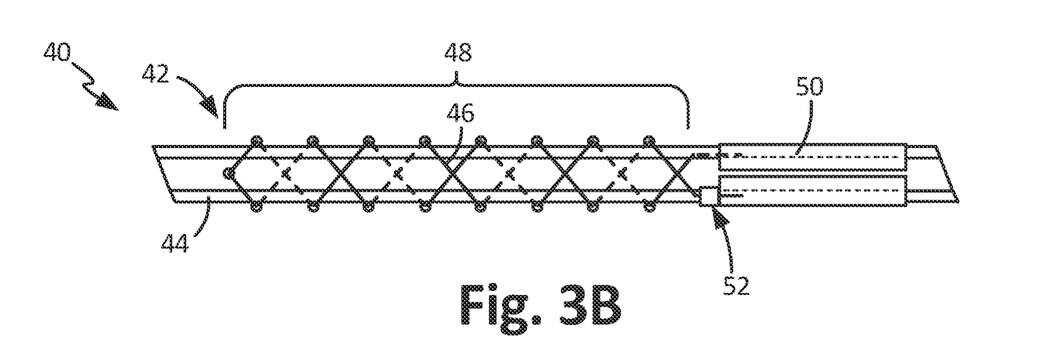
FIG. 3B is a top view of the assembly of FIG. 3A.

FIGS. 3A and 3B depict another exemplary embodiment of an assembly 40 having a resonant marker 42 constructed on an endovascular catheter 44. In addition to having a conductor 46 (that forms into a coil 48) and a capacitor 50, the marker 42 also has a resistor 52 coupled to the conductor 46 and the capacitor 50 as shown. The resistor 52 can be used to alter the performance or functionality of the resonator 42. According to certain implementations, the resistor 52 can be, but is not limited to, a discrete ceramic surface mount resistor, thin or thick film resistive material, or a reduced path width of a conductor. In certain instances, control or selective modification of the resistance via the resistor allows for control over the bandwidth of the marker's resonant frequency response. Thus, the bandwidth of the marker's response can be adjusted via adjustment of the resistor. Modification of the bandwidth can be advantageous to correct for different inductive loading conditions experienced within the patient's body.

Figure 4:
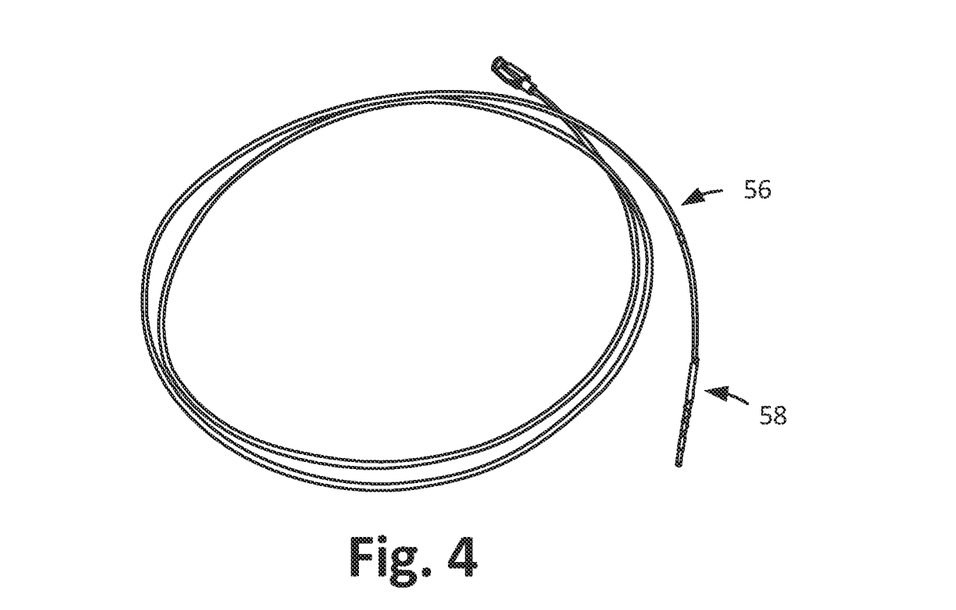
FIG. 4 is a perspective view of an assembly having two resonant markers positioned around a catheter, according to one embodiment.

One example of a catheter 54 with two markers 56, 58 is depicted in FIG. 4. It is understood that the two markers 56, 58 can be any of the marker embodiments disclosed or contemplated herein.

The various resonant marker embodiments disclosed herein for use in the MRI process has substantial advantages over previously known technologies. Traditional interventional procedures performed under X-ray fluoroscopy typically use radiopaque markers (which are typically made of high atomic number metals) to locate catheters and other devices, thus distinguishing them from adjacent vasculature. Although X-ray fluoroscopy is the current state of the art guidance method for most interventional procedures, it is limited to visualizing the lumens of blood vessels (made radiopaque by intravascular injection of iodinated contrast) and delivers a significant ionizing radiation dose to patients and medical practitioners. MRI offers a variety of advantages over X-ray fluoroscopy, including superior soft tissue resolution as well as physiologic measures of parameters including tissue perfusion and infarction (diffusion). MRI guidance for interventional procedures has traditionally been limited by slow image refresh rates compared to X-ray, but this has been largely overcome in the past decade by the vast improvements in processing power.

A persistent barrier to adoption of MRI guidance for interventional procedures is the difficulty visualizing catheters and other interventional devices in magnetic resonance images in real-time. Both passive and active catheter-tracking techniques have been developed, the former typically involving paramagnetic metal markers and the latter involving resonators or capacitors. Although passive catheter-tracking techniques are often dependent of the orientation of the imaged device, active methods are usually orientation-independent. Multiple interventional catheter systems for the MR environment have been proposed and are under development, however, an optimized catheter-integrated tracking method is required.

The various embodiments of catheter-integrated devices and related methods disclosed or contemplated herein fill that need. The resonant marker embodiments herein can be used for interventional procedures that benefit from the enhanced structural and physiologic visualization afforded by MRI. Hospitals with dual X-ray fluoroscopy MRI (XMR) suites can navigate using traditional methods under X-ray fluoroscopy and image under MR to analyze the efficacy of treatments mid-procedure. With additional development of catheters and other interventional devices for use under MRI guidance, the disclosed system implementations provide a platform for enhanced operator visualization during manual and computer-aided navigation.

In use, marker embodiments such as the marker 12 depicted in FIGS. 1A and 1B and discussed above are inserted into a patient while the patient is being monitored by magnetic resonance imaging (MRI) so as to visualize the location of the marker in vivo.

Prior to use, in certain embodiments, the marker (such as marker 12 discussed above) can be "tuned" to match the frequency of the MRI scanner being used. More specifically, the capacitor (such as the capacitor 18 described above) is configured such that it can be trimmed if necessary to reduce capacitance until the assembly 10 resonates at the desired frequency. In other instances, the capacitor may also be tuned using such processes as, but not limited to, laser trimming or selective etching. In these embodiments, the resonant marker can be initially fabricated to resonate at a lower frequency than desired and have a capacitor (such as capacitor 18) that can be trimmed to reduce capacitance and thus raise the frequency until the assembly (such as assembly 10) resonates at the desired frequency. In other arrangements, the marker may also be tuned by altering coil length and/or geometry via the addition of a close-fitting conductive ring on the double helical coil.

When placed inside the MRI scanner, the inductive coil created by the wire 16 couples with the pulsing B1 field during imaging. The resonant frequency is tuned to match the Larmor frequency of the particular MRI scanner being used (e.g., about 127.72 MHz for 3T scanners; 63.86 MHz for 1.5T scanners, depending on the manufacturer) by changing the available capacitance, inductance, or resistance e as described above, effectively matching the resonant frequency of the marker to that of the scanner.

In certain embodiments, the MRI imaging can be performed at 3T using a spoiled gradient echo sequence with a 2° flip angle. Alternatively, other magnetic inductivities and configurations well-known in the art are possible. Each of the various marker embodiments disclosed and contemplated herein has the ability to 'over flip' at higher flip angles or different pulse sequences such that it may disappear when desired. This is advantageous to get unobstructed high-resolution images of the target tissues or portions of the patient's body when catheter tracking is not being performed.

Figure 8:
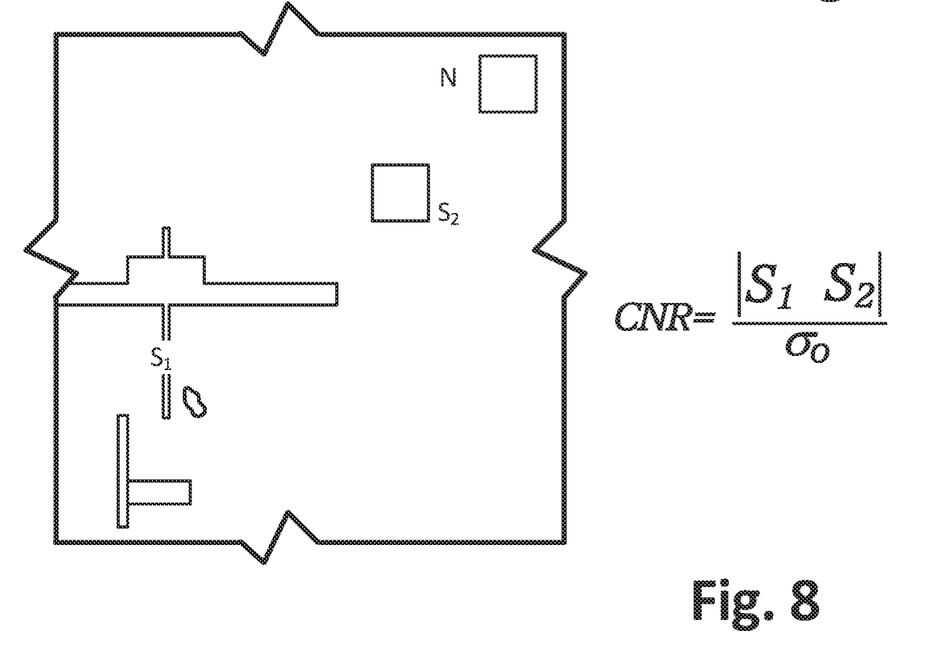
FIG. 8 is an image of a tuned resonant marker resonating at 3T, wherein the contrast to noise ratio ("CNR") is calculated from the resulting images.

As can be observed in FIGS. 8-10 (discussed below in further detail), these exemplary embodiments provide interventionists with bright and highly localized signal enhancements at its location along a catheter or other interventional device. This device-integrated design is safe, effective, robust and fully biocompatible. Due to its highly localized nature, the high signal enhancement does not degrade imaging of neighboring tissues at higher flip angles. High imaging frame rate and low flip angle visibility allows for real-time navigation with the resonator.

Further marker embodiments are depicted in FIGS. 5A-6B. In these embodiments, the various markers as shown have been designed such that they can be formed or otherwise created from a stock flexible circuit board substrate using pre-existing manufacturing techniques in order to make a reproducible, reliable and tunable resonant marker. Production of these resonant marker embodiments via high-density flexible circuit technology allows for more reliable and predictable frequency selection for both 3T and 1.5T.

Figure 5A:
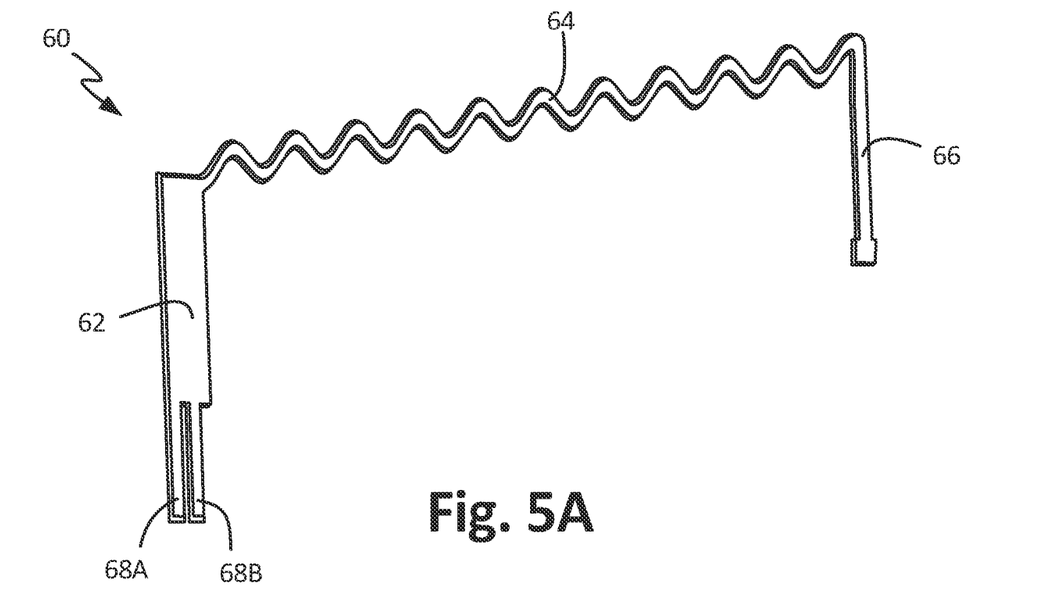
FIG. 5A is front side view of a resonant solenoid marker prior to assembly, according to one embodiment.
Figure 5B:
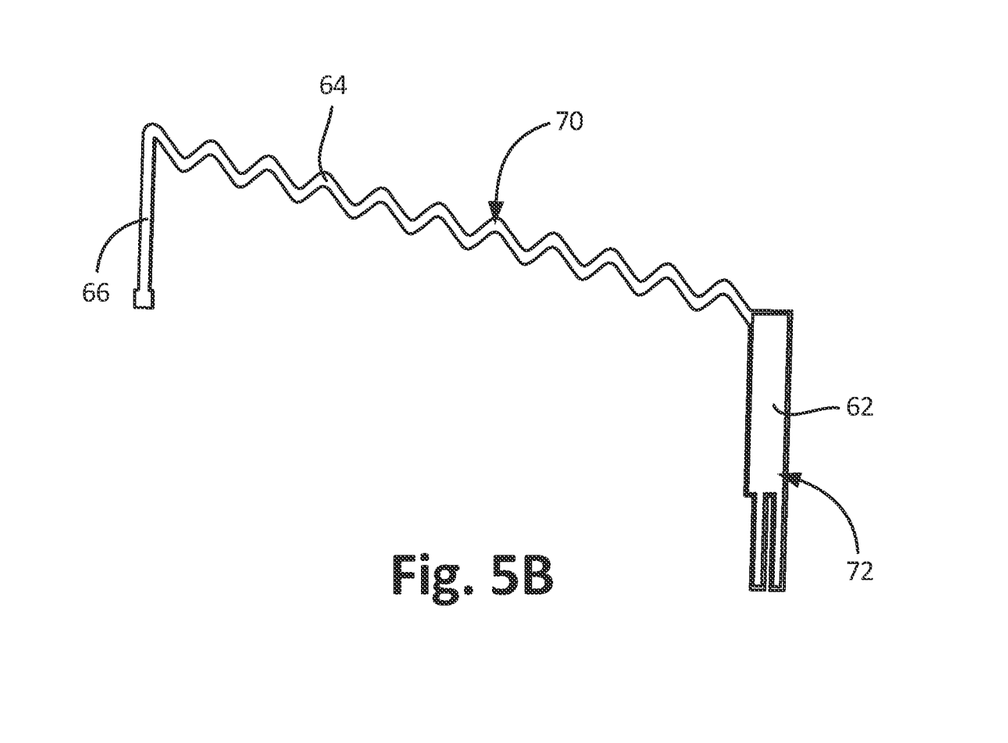
FIG. 5B is a rear side view of the resonant marker of FIG. 5A.

For example, FIGS. 5A and 5B depict the front view (FIG. 5A) and the rear view (FIG. 5B) of a marker 60 having a capacitor 62, a trace 64, and a return trace component 66. As shown, the marker 60 is in its manufactured configuration (also referred to as its "pre-placement configuration") prior to being positioned on a catheter. The return trace component 66 is configured to contact the capacitor 62 when the marker 60 is positioned on a catheter (not shown). The capacitor 62 has two extensions 68A, 68B (also referred to as "tails" or "smaller capacitors"). According to one embodiment, a user can remove or otherwise eliminate (also referred to as "trimming") a portion of either or both of the extensions 68A, 68B in order to tune the capacitor 62 as discussed elsewhere herein once the marker 60 is placed on the target catheter. The extensions 68A, 68B are included to allow for smaller tuning adjustments as a result of the trimming process in comparison to the adjustments that take place as a result of trimming the capacitor 62 itself, thereby providing additional accuracy to the tuning process.

The trace 64 is configured to form into a solenoid configuration (a specific type of coil configuration) when the trace 64 is positioned around the target catheter. When positioned on the catheter, the trace 64 in the solenoid configuration extends along the catheter length and the return trace 66 extends back toward the capacitor 62 such that the distal end of the return trace 66 contacts the capacitor 62.

As shown in FIG. 5B, the rear or "back" of the marker 60 has a backing or insulating cover layer 70 on the trace 64 and a copper layer 72 on the back portion of the capacitor 62. The backing 70 provides insulation for the trace 64 when the marker 60 has been positioned on the target catheter. The copper layer 72 acts as the back, or second, plate of the parallel plate capacitor 62 and conductive pad on which to affix the return trace 66. This may be made out of the same or different material as discussed above for the conductor embodiments.

Figure 6A:
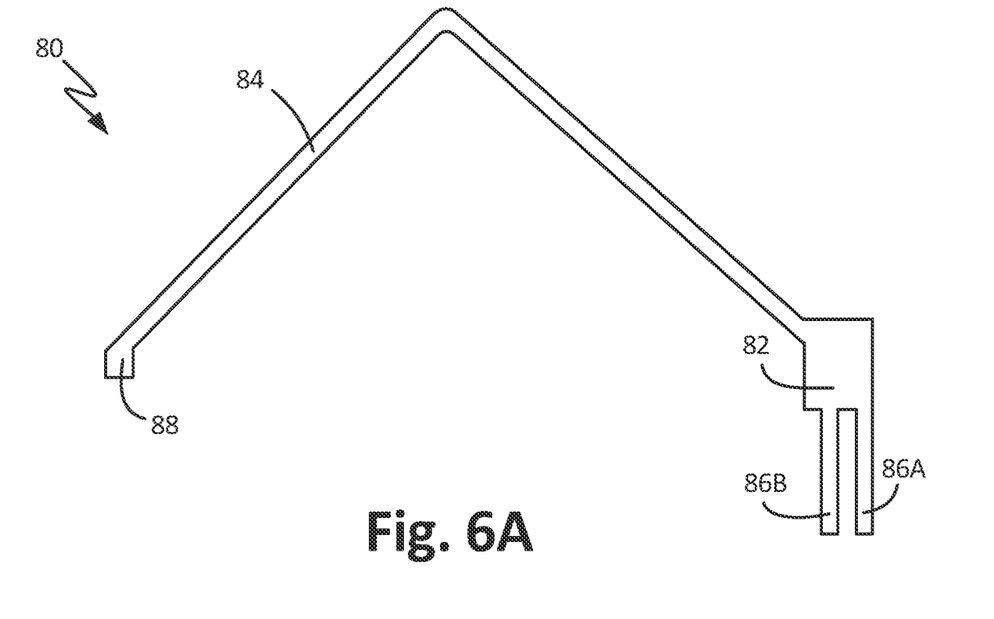
FIG. 6A is a front side view of a resonant double helical marker prior to assembly, according to one embodiment.
Figure 6B:
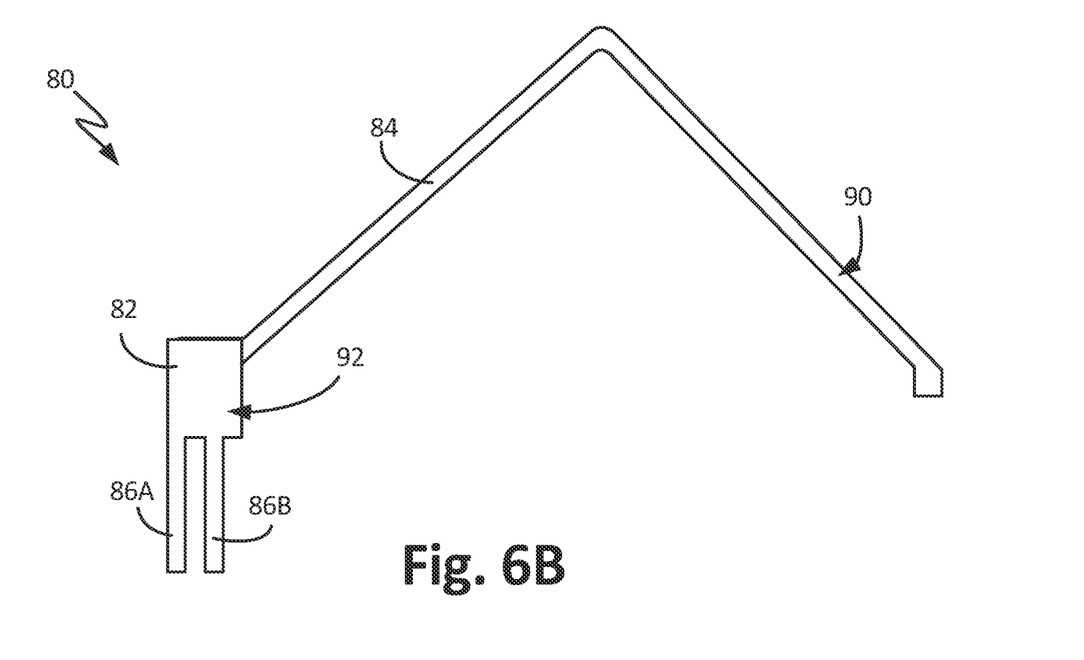
FIG. 6B is a rear side view of the resonant marker of FIG. 6A.

FIGS. 6A and 6B depict the front view (FIG. 6A) and the rear view (FIG. 6B) of another marker 80 embodiment having a capacitor 82 and a trace 84. As shown, the marker 80 is in its manufactured configuration prior to being positioned on a catheter. Like the marker 60 above, the capacitor 82 has two extensions 86A, 86B which have the same purpose in this embodiment. The trace 84 is configured to form into a double helix configuration when the trace 84 is positioned around the target catheter. When positioned on the catheter, a portion of the trace 84 in the double helix configuration extends along the catheter length and another portion extends back toward the capacitor 82 such that the distal end 88 of the trace 84 contacts the capacitor 82.

As shown in FIG. 6B, the rear or "back" of the marker 80 has a backing or insulating cover layer 90 on the trace 84 and a copper layer 92 on the back portion of the capacitor 82. The backing 90 provides insulation for the trace 84 when the marker 80 has been positioned on the target catheter. The copper layer 92 acts as the second plate of the parallel plate capacitor 82 and conductive pad on which to affix the distal end 88 of the double helix trace 84.

The two designs are aimed at optimizing coupling to the B1 field at all angles within the MR scanner.

In these embodiments as set forth in FIGS. 5A-6B and discussed above, it is understood that these resonators can have the same features and attributes as the marker 12 embodiment discussed above and depicted in FIGS. 1A and 1B.

Various implementations include several variables so as to optimize the overall usability between capacitor length, inductor shape (helical/sinusoidal) and length. For each inductor shape, various distinct capacitor and inductor lengths have been utilized to cover a spectrum of possible frequencies to adjust for loading (immersion in fluid/catheter substrate) and other unaccounted variables as desired.

Certain implementations comprise components from Sierra Circuits (www.protoexpress.com), such as flexible circuits on a polyimide substrate. Certain implementations comprise the following fabrication specifications for the base copper-polyimide-copper laminate provided by DuPont: Material: DuPont Pyralux AP8515R; 0.001" Polyimide with ½ oz copper 2 sides. Note that this material does not have acrylic adhesive adding to the thickness, the PI is bonded directly to copper. Finished Thickness: Nominal 0.0024" or 61 microns. Controlled capacitance structures based on 1-mil polyimide between copper layers. [No adhesive layers in this material]. Thickness Tolerance: +/−10% or +/−6 microns. Surface Finish: Bare Copper. Starting Copper Outer: As supplied by ½ oz DuPont Pyralux. Outer Layer Finish Copper: none. Inner Copper: None. As would be apparent to one of skill in the art, other configurations are possible.

The disclosed devices, systems and methods have implications in a wide array of endovascular procedures, in surgical deep brain stimulation, guided biopsies and guided drug delivery technologies, amongst others. Exemplary endovascular applications for the disclosed include ischemic stroke treatment (perfusion/diffusion analysis), blood clot evacuation, cerebral aneurysm embolization, arteriovenous malformation or fistula embolization, cerebral vasospasm treatment, emolic delivery to tumors (meningiomas; malignant tumors of the brain, head, neck, and spine), tumor ablation, transarterial chemoembolization, cardiac arrhythmia ablation, and other coronary interventions, as well as therapeutic embolization of tumors, selective drug delivery, transarterial chemoembolization, and cardiac arrhythmia ablations, amongst others.

Nonvascular minimally invasive percutaneous procedures including biopsy, tumor ablation, and device implantation could also benefit from more robust visualization of interventional devices under MRI guidance. Biopsies of cancerous lesions or inflammatory diseases currently guided by x-ray computed tomography (CT) could be replaced by MR guided procedures. Improved tissue differentiation by MRI allows for more accurate placement and guidance of surgical instruments and implants under real-time visualization of the region of interest without exposing patients or operators to high levels of ionizing radiation.

For example, treatment of Parkinson's through deep brain stimulation (DBS) using the ClearPoint® system under MRI guidance increases tip precision and efficacy while decreasing procedure time and reducing radiation exposure to zero. The Disclosed system provides an opportunity to expand and develop MR guided procedures such as biopsies, drug delivery, focal laser ablation and implantations that may be aided by improved visualization of devices intraprocedurally.

EXAMPLES

Example 1

Figure 7:
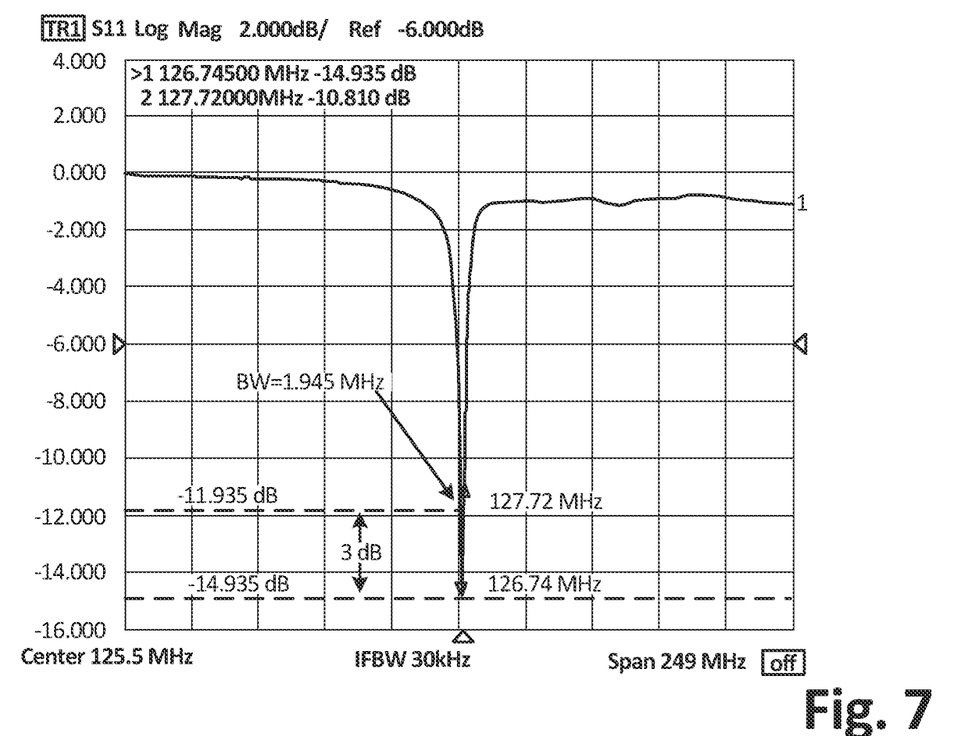
FIG. 7 is a graph depicting a tuned marker resonating at 126.74 MHz, which is close to the B1 frequency of 127.72 MHz (3T magnet), wherein the marker is coupled to a custom H-filed probe for testing, according to one embodiment.

Materials and Methods. Experiments were performed on the above marker embodiment at 3T (Discovery MR750w 3.0T, General Electric, Fairfield, CT) using a spoiled gradient echo sequence with a 2° flip angle (TE/TR=1.8/5.6 ms, square 32 mm FOV, slice thickness 5 mm, matrix 256×128). The resonant markers were positioned in parallel with B0 in a water phantom. The contrast-to-noise ratio (CNR) was calculated using OsiriX Viewer. Coils were immersed in water and tuned with a network analyzer (Agilent Technologies 300 kHz-1.5 GHz ENA Series) and custom H-filed probe that coupled wirelessly to the resonant structure, as can be seen in FIG. 7.

Results. FIG. 8 depicts the resulting image. In FIG. 8, the tuned resonant marker resonates at 3T, wherein the micro resonant marker was clearly visible with a bright and highly localized signal enhancement. The signal did not contaminate adjacent tissue. The complete resonant structure had a maximum diameter of 1.95 mm (<6 French) and a length 8 mm. The coil had a calculated Q of 106.11 (FIG. 7) and a CNR of 45.427 (FIG. 8).

Conclusion. The present study was developed to validate certain micro resonant marker embodiments for endovascular catheter navigation under MR guidance. The passive structure of the embodiments disclosed herein allows for tracking of sub 6 French endovascular catheters. The disclosed micro-resonance marker provides an opportunity for safe and accurate catheter tracking and the ability to capitalize on the wealth of physiologic and structural information afforded by the interventional MRI environment. In various embodiments, the marker's flexible structure and localized resonance make it a viable marker for MR guided catheter navigation.

Example 2

Figure 9:
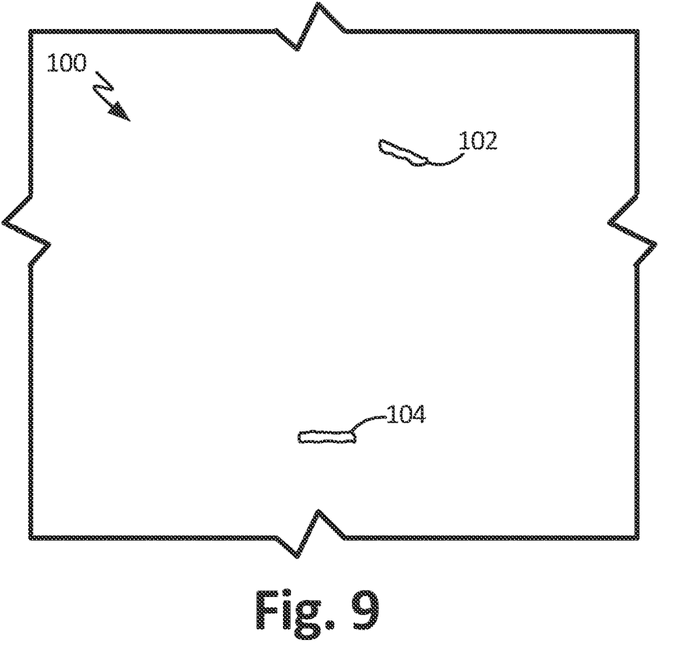
FIG. 9 is an image of two tuned resonant markers resonating at 1.5T, according to one embodiment.

FIG. 9 depicts an image 100 of two resonant markers 102, 104 on catheters (not visible in the image). The markers 102, 104 were imaged using a Phillips 1.5T MRI (~68.899509 MHz at time of acquisition). A 1° flip angle (FA) Gradient Echo sequence was used to generate highly localized signal enhancement. In this exemplary embodiment, the markers 102, 104 are clearly visible at multiple orientations when placed into a water phantom. It can be observed that all darker areas are either water or the catheter on which the markers 102, 104 were placed. MR spectroscopy using magnetic field gradients allows for acquisition of three-dimensional coordinates of the marker in the bore of the magnet.

Example 3

Figure 10:
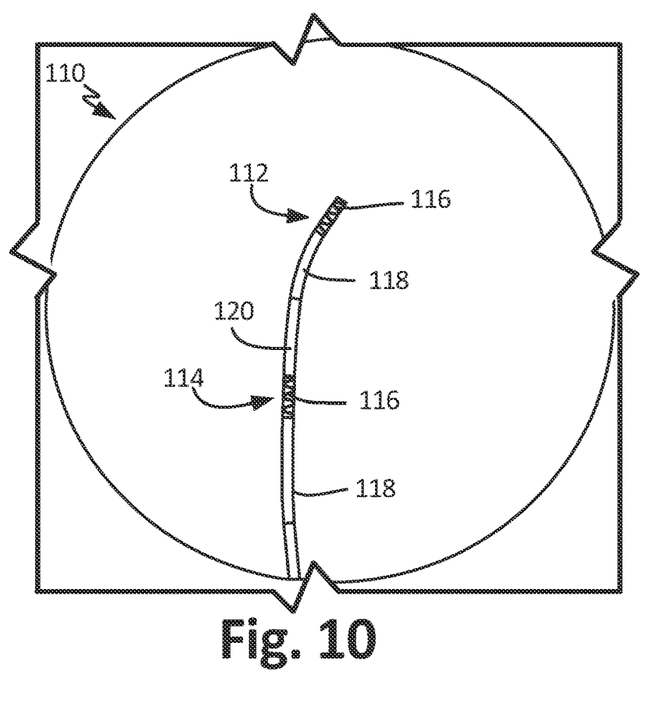
FIG. 10 is an image of two resonant markers on a catheter imaged using X-ray fluoroscopy, according to one embodiment.

An image 110 is depicted in FIG. 10 using X-ray fluoroscopy (C-Arm at China Basin), according to one exemplary embodiment. More specifically, this catheter has two markers 112, 114 positioned thereon acting as radiopaque markers 112, 114 for procedures requiring X-ray fluoroscopy. As can be seen in the figure, the markers 112, 114 each have coils 116 and capacitors 118 that are clearly visible using the X-ray fluoroscopy technology compared to the nearly transparent main catheter body 120.

Example 4

Figure 11:
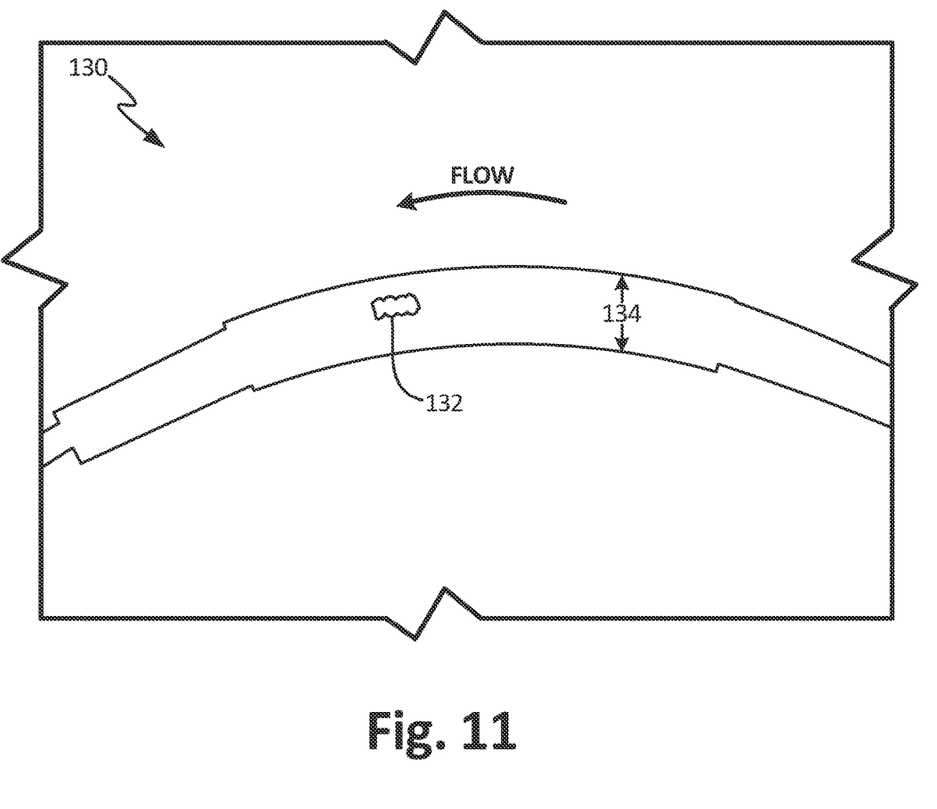
FIG. 11 is an image of a resonant marker in an aortic flow model at 3T, according to one embodiment.

An MRI image 130 is depicted in FIG. 11 showing an Aortic Flow Model (GE 3TWB at China Basin) with a replicated aorta 134. In this example, high flow rates were applied through the replicated aorta 134. In this instance, the fluid is flowing from right to left. As can be seen in the figure, despite the high flow rates, the marker 132 is clearly visible using MRI technology. The marker 132 does not suffer from distortion or signal loss, and does not propagate into surrounding regions.

Although the disclosure has been described with reference to preferred embodiments, persons skilled in the art will recognize that changes may be made in form and detail without departing from the spirit and scope of the disclosed apparatus, systems and methods.

What is claimed is:

1. An omnidirectional magnetic resonance imaging ("MRI") resonant marker, comprising:
   a) a tunable capacitor comprising a first flexible circuit laminate; and
   b) a conductor coil comprising a second flexible circuit laminate comprising:
      a first trace portion operably coupled to the tunable capacitor, and
      a second trace portion operably coupled to the first trace portion opposite from the tunable capacitor,
wherein the second flexible circuit laminate is configured to wrap around a medical device to form the conductor coil in which the first trace portion extends away from the tunable capacitor and the second trace portion extends back toward the tunable capacitor such that a distal end of the second trace portion operably couples to the tunable capacitor.

2. The resonant marker of claim 1, wherein the tunable capacitor is tunable by modifying the tunable capacitor structurally or chemically.

3. The resonant marker of claim 1, further comprising an outer sealant layer disposed over the tunable capacitor and the conductor coil.

4. The resonant marker of claim 1, further comprising a resistor operably coupled to the tunable capacitor and the conductor coil.

5. The resonant marker of claim 1, further comprising an insulating layer on one side of the conductor.

6. The resonant marker of claim 1, wherein the first flexible circuit laminate is integral with the second flexible circuit laminate.

7. The resonant marker of claim 1, wherein the medical device is a catheter.

8. An omnidirectional MRI resonant marker, comprising:
   a) a tunable capacitor comprising first and second contacts; and
   b) a conductor coil operably coupled to the tunable capacitor, the conductor coil comprising a flexible circuit laminate comprising a first trace portion operably coupled to the first contact and extending away from the tunable capacitor, and a second trace portion operably coupled to the first trace portion opposite from the tunable capacitor, wherein the second trace portion extends back toward the tunable capacitor such that a distal end of the second trace portion operably couples to the second contact, and wherein at least one of the first and second trace portions comprises a plurality of windings configured to wrap around a medical device to form at least part of the conductor coil.

9. The resonant marker of claim 8, wherein the conductor coil is configured to be positioned around a catheter.

10. The resonant marker of claim 8, wherein the conductor coil is disposed within a wall of a catheter.

11. The resonant marker of claim 8, further comprising an outer sealant layer disposed over the tunable capacitor and the conductor coil.

12. The resonant marker of claim 8, further comprising a resistor operably coupled to the tunable capacitor and the conductor coil.

13. The resonant marker of claim 8, wherein the tunable capacitor is tunable through structural.

14. The resonant marker of claim 1, wherein the conductor coil comprises a plurality of windings of the first trace portion and a plurality of windings of the second trace portion overlapping the plurality of windings of the first trace portion.

15. The resonant marker of claim 1, wherein the conductor coil comprises a plurality of windings of the first trace portion and wherein the second trace portion extends back to the tunable capacitor without winding.

16. The resonant marker of claim 15, wherein the first trace portion comprises an undulating shape.

17. The resonant marker of claim 8, wherein the first and second trace portions each comprise a plurality of windings.

18. The resonant marker of claim 8, wherein the first trace portion comprises a plurality of windings and the second trace portion extends back to the tunable capacitor without winding.

19. An omnidirectional MRI trackable catheter, comprising:
   a) a catheter body comprising a wall defining a lumen;
   b) a tunable capacitor comprising a first flexible circuit laminate; and
   c) a conductor coil comprising a second flexible circuit laminate comprising:
      a first trace portion operably coupled to the tunable capacitor and comprising a plurality of windings around the lumen, and
      a second trace portion operably coupled to the first trace portion opposite from the tunable capacitor;
   wherein the first trace portion extends away from the tunable capacitor and the second trace portion extends back toward the tunable capacitor and a distal end of the second trace portion is operably coupled to the tunable capacitor.

20. The trackable catheter of claim 19, wherein the second trace portion comprises a plurality of windings overlapping the plurality of windings of the first trace portion.

* * * * *